(12) United States Patent
Chen et al.

(10) Patent No.: US 6,921,761 B2
(45) Date of Patent: Jul. 26, 2005

(54) GONADOTROPIN-RELEASING HORMONE RECEPTOR ANTAGONISTS AND METHODS RELATING THERETO

(75) Inventors: Chen Chen, San Diego, CA (US); Dongpei Wu, San Diego, CA (US); Zhiqiang Guo, San Diego, CA (US); Martin Rowbottom, San Diego, CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 0 days.

(21) Appl. No.: 10/832,092

(22) Filed: Apr. 26, 2004

(65) Prior Publication Data

US 2004/0266773 A1 Dec. 30, 2004

Related U.S. Application Data

(63) Continuation of application No. 10/211,972, filed on Aug. 2, 2002, now Pat. No. 6,750,350.
(60) Provisional application No. 60/310,019, filed on Aug. 2, 2001.

(51) Int. Cl.[7] .................. C07D 237/14; A61K 31/50; A61K 31/51; A61P 35/00
(52) U.S. Cl. .................. 514/247; 514/252.01; 544/238; 544/247
(58) Field of Search .................. 544/224, 238; 514/247, 252.01

(56) References Cited

U.S. PATENT DOCUMENTS

| 5,780,437 A | 7/1998 | Goulet et al. .................. 514/19 |
| 5,849,764 A | 12/1998 | Goulet et al. .................. 514/337 |

FOREIGN PATENT DOCUMENTS

| WO | WO 96/38438 | 12/1996 |
| WO | WO 97/14682 | 4/1997 |
| WO | WO 97/14697 | 4/1997 |
| WO | WO 97/21435 | 6/1997 |
| WO | WO 97/21703 | 6/1997 |
| WO | WO 97/21704 | 6/1997 |
| WO | WO 97/21707 | 6/1997 |
| WO | WO 97/44037 | 11/1997 |
| WO | WO 97/44041 | 11/1997 |
| WO | WO 97/44321 | 11/1997 |
| WO | WO 97/44339 | 11/1997 |
| WO | WO 98/55116 | 12/1998 |
| WO | WO 98/55119 | 12/1998 |
| WO | WO 98/55470 | 12/1998 |
| WO | WO 98/55479 | 12/1998 |
| WO | WO 99/09033 | 2/1999 |
| WO | WO 99/33831 | 7/1999 |
| WO | WO 00/56739 | 9/2000 |
| WO | WO 01/29044 | 4/2001 |
| WO | WO 01/55119 | 8/2001 |

OTHER PUBLICATIONS

Wolft Manfred E. "Burger's Medicinal Chemistry, 5ed, Part 1", John Wiley & Sons, 1995, pp. 975–977.*
Banker, G.S. et al, "Modern Pharmaceutics, 3ed.", Marcel Dekker, New York. 1996, pp. 451 and 596.*
Cecil Textbook of Medicine, edited by Bennet, J.C., and Plum F., 20th edition, vol. 1, 1004–1010, 1996.*
Huirne, JA, and Lambalk, GB., Lancet 358(9295): 1793–1803, 2001.*
Cho et al., "Discovery of a novel, potent, and orally active nonpeptide antagonist of the human luteinizing hormone-releasing hormone (LHRH) receptor,"*J Med Chem. 41*(22): 4190–4195, Oct. 22, 1998.
Huirne, J., et al., *Lancet 358*(9295):1793–1803, 2001.

* cited by examiner

*Primary Examiner*—Venkataraman Balasubramanian
(74) *Attorney, Agent, or Firm*—Seed IP Law Group PLLC

(57) ABSTRACT

GnRH receptor antagonists are disclosed which have utility in the treatment of a variety of sex-hormone related conditions in both men and women. The compounds of this invention have the structure:

wherein A, $R_1$, $R_2$, $R_{3a}$, $R_{3b}$, $R_4$, $R_5$, $R_6$, and n are as defined herein, including stereoisomers, prodrugs and pharmaceutically acceptable salts thereof. Also disclosed are compositions containing a compound of this invention in combination with a pharmaceutically acceptable carrier, as well as methods relating to the use thereof for antagonizing gonadotropin-releasing hormone in a subject in need thereof.

20 Claims, No Drawings

GONADOTROPIN-RELEASING HORMONE RECEPTOR ANTAGONISTS AND METHODS RELATING THERETO

CROSS-REFERENCES TO RELATED APPLICATIONS

This application is a continuation of U.S. application Ser. No. 10/211,972 filed Aug. 2, 2002, now U.S. Pat. No. 6,750,350 which claims the benefit of U.S. Provisional Patent Application No. 60/310,019 filed Aug. 2, 2001, which applications are incorporated herein by reference in their entireties.

STATEMENT REGARDING FEDERALLY SPONSORED RESEARCH OR DEVELOPMENT

Partial funding of the work described herein was provided by the U.S. Government under Grant No. R43-HD38625 provided by the National Institute of Health. The U.S. Government may have certain rights in this invention.

BACKGROUND OF THE INVENTION

1. Field of the Invention

This invention relates generally to gonadotropin-releasing hormone (GnRH) receptor antagonists, and to methods of treating disorders by administration of such antagonists to a warm-blooded animal in need thereof.

2. Description of the Related Art

Gonadotropin-releasing hormone (GnRH), also known as luteinizing hormone-releasing hormone (LHRH), is a decapeptide (pGlu-His-Trp-Ser-Tyr-Gly-Leu-Arg-Pro-Gly-NH$_2$) that plays an important role in human reproduction. GnRH is released from the hypothalamus and acts on the pituitary gland to stimulate the biosynthesis and release of luteinizing hormone (LH) and follicle-stimulating hormone (FSH). LH released from the pituitary gland is responsible for the regulation of gonadal steroid production in both males and females, while FSH regulates spermatogenesis in males and follicular development in females.

Due to its biological importance, synthetic antagonists and agonists to GnRH have been the focus of considerable attention, particularly in the context of prostate cancer, breast cancer, endometriosis, uterine leiomyoma, and precocious puberty. For example, peptidic GnRH agonists, such as leuprorelin (pGlu-His-Trp-Ser-Tyr-D-Leu-Leu-Arg-Pro-NHEt), have been used to treat such conditions. Such agonists appear to function by binding to the GnRH receptor in the pituitary gonadotropins, thereby inducing the synthesis and release of gonadotropins. Chronic administration of GnRH agonists depletes gonadotropins and subsequently down-regulates the receptor, resulting in suppression of steroidal hormones after some period of time (e.g., on the order of 2–3 weeks following initiation of chronic administration).

In contrast, GnRH antagonists are believed to suppress gonadotropins from the onset, and thus have received the most attention over the past two decades. To date, some of the primary obstacles to the clinical use of such antagonists have been their relatively low bioavailability and adverse side effects caused by histamine release. However, several peptidic antagonists with low histamine release properties have been reported, although they still must be delivered via sustained delivery routes (such as subcutaneous injection or intranasal spray) due to limited bioavailability.

In view of the limitations associated with peptidic GnRH antagonists, a number of nonpeptidic compounds have been proposed. For example, Cho et al. (*J. Med. Chem.* 41:4190–4195, 1998) discloses thieno[2,3-b]pyridin-4-ones for use as GnRH receptor antagonists; U.S. Pat. Nos. 5,780,437 and 5,849,764 teach substituted indoles as GnRH receptor antagonists (as do published PCTs WO 97/21704, 98/55479, 98/55470, 98/55116, 98/55119, 97/21707, 97/21703 and 97/21435); published PCT WO 96/38438 discloses tricyclic diazepines as GNRH receptor antagonists; published PCTs WO97/14682, 97/14697 and 99/09033 disclose quinoline and thienopyridine derivatives as GNRH antagonists; published PCTs WO 97/44037, 97/44041, 97/44321 and 97/44339 teach substituted quinolin-2-ones as GnRH receptor antagonists; and published PCT WO 99/33831 discloses certain phenyl-substituted fused nitrogen-containing bicyclic compounds as GnRH receptor antagonists.

While significant strides have been made in this field, there remains a need in the art for effective small molecule GNRH receptor antagonists. There is also a need for pharmaceutical compositions containing such GNRH receptor antagonists, as well as methods relating to the use thereof to treat, for example, sex-hormone related conditions. The present invention fulfills these needs, and provides other related advantages.

BRIEF SUMMARY OF THE INVENTION

In brief, this invention is generally directed to gonadotropin-releasing hormone (GnRH) receptor antagonists, as well as to methods for their preparation and use, and to pharmaceutical compositions containing the same. More specifically, the GnRH receptor antagonists of this invention are compounds having the following general structure (I):

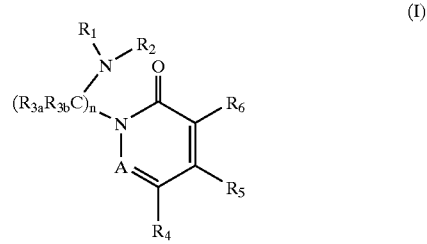

including stereoisomers, prodrugs and pharmaceutically acceptable salts thereof, wherein A, $R_1$, $R_2$, $R_{3a}$, $R_{3b}$, $R_4$, $R_5$, $R_6$, and n are as defined below.

The GNRH receptor antagonists of this invention have utility over a wide range of therapeutic applications, and may be used to treat a variety of sex-hormone related conditions in both men and women, as well as a mammal in general (also referred to herein as a "subject"). For example, such conditions include endometriosis, uterine fibroids, polycystic ovarian disease, hirsutism, precocious puberty, gonadal steroid-dependent neoplasia such as cancers of the prostate, breast and ovary, gonadotrophe pituitary adenomas, sleep apnea, irritable bowel syndrome, premenstrual syndrome, benign prostatic hypertrophy, contraception and infertility (e.g., assisted reproductive therapy such as in vitro fertilization). The compounds of this invention are also useful as an adjunct to treatment of growth hormone deficiency and short stature, and for the treatment of systemic lupus erythematosis. The compounds are also useful in combination with androgens, estrogens, progesterones, and antiestrogens and antiprogestogens for the treatment of endometriosis, fibroids, and in contraception, as well as in combination with an angiotensin-converting enzyme inhibitor, an angiotensin II-receptor antagonist, or a renin inhibitor for the treatment of uterine fibroids. In addition, the compounds may be used in combination with bisphosphonates and other agents for the treatment and/or prevention of disturbances of calcium, phosphate and bone metabolism, and in combination with estrogens, progesterones and/or androgens for the prevention or treatment of bone loss or hypogonadal symptoms such as hot flashes during therapy with a GnRH antagonist.

The methods of this invention include administering an effective amount of a GNRH receptor antagonist, preferably in the form of a pharmaceutical composition, to a mammal in need thereof. Thus, in still a further embodiment, pharmaceutical compositions are disclosed containing one or more GnRH receptor antagonists of this invention in combination with a pharmaceutically acceptable carrier and/or diluent.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION OF THE INVENTION

As mentioned above, the present invention is directed generally to compounds useful as gonadotropin-releasing hormone (GnRH) receptor antagonists. The compounds of this invention have the following structure (I):

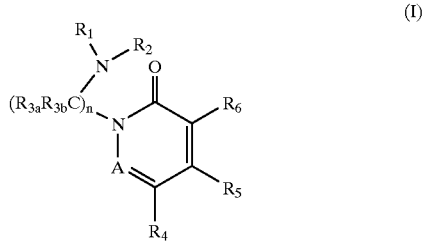

including stereoisomers, prodrugs and pharmaceutically acceptable salts thereof,
wherein:

A is N or $CR_7$;

n is 2, 3 or 4;

$R_1$ and $R_2$ are the same or different and independently hydrogen, alkyl, substituted alkyl, aryl, substituted aryl, arylalkyl, substituted arylalkyl, heterocycle, substituted heterocycle, heterocyclealkyl, substituted heterocyclealkyl, —$C(R_8)(=NR_9)$ or —$C(NR_{10}R_{11})(=NR_9)$;

or $R_1$ and $R_2$ taken together with the nitrogen atom to which they are attached form a heterocycle or a substituted heterocycle;

$R_{3a}$ and $R_{3b}$ are the same or different and, at each occurrence, independently hydrogen, alkyl, substituted alkyl, alkoxy, alkylthio, alkylamino, aryl, substituted aryl, arylalkyl, substituted arylalkyl, heterocycle, substituted heterocycle, heterocyclealkyl, substituted heterocyclealkyl, —$COOR_{12}$ or —$CONR_{10}R_{11}$;

or $R_{3a}$ and $R_{3b}$ taken together with the carbon atom to which they are attached form a homocycle, substituted homocycle, heterocycle or substituted heterocycle;

or $R_{3a}$ and the carbon to which it is attached taken together with $R_1$ and the nitrogen to which it is attached form a heterocycle or substituted heterocycle;

$R_4$ is arylalkyl, substituted arylalkyl, heteroarylalkyl or substituted heteroarylalkyl;

$R_5$ is hydrogen, alkyl, or substituted alkyl;

$R_6$ is aryl, substituted aryl, heteroaryl, or substituted heteroaryl;

$R_7$ is hydrogen, alkyl, or substituted alkyl;

$R_8$ is independently hydrogen, alkyl, substituted alkyl, aryl, substituted aryl, arylalkyl, substituted arylalkyl, heterocycle, substituted heterocycle, heterocyclealkyl or substituted heterocyclealkyl;

$R_9$ is independently hydrogen, alkyl, substituted alkyl, aryl, substituted aryl, arylalkyl, substituted arylalkyl, heterocycle, substituted heterocycle, heterocyclealkyl or substituted heterocyclealkyl;

$R_{10}$ and $R_{11}$ are the same or different independently hydrogen, alkyl, substituted alkyl, aryl, substituted aryl, arylalkyl, substituted arylalkyl, heterocycle, substituted heterocycle, heterocyclealkyl or substituted heterocyclealkyl; and $R_{12}$ is hydrogen, alkyl, or substituted alkyl.

As used herein, the above terms have the following meaning:

"Alkyl" means a straight chain or branched, noncyclic or cyclic, unsaturated or saturated aliphatic hydrocarbon containing from 1 to 10 carbon atoms, while the term "lower alkyl" has the same meaning as alkyl but contains from 1 to 6 carbon atoms. The term "higher alkyl" has the same meaning as alkyl but contains from 2 to 10 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cyclic alkyls are also referred to herein as a "homocycles" or "homocyclic rings." Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"Aryl" means an aromatic carbocyclic moiety such as phenyl or naphthyl.

"Arylalkyl" means an alkyl having at least one alkyl hydrogen atoms replaced with an aryl moiety, such as benzyl, —$(CH_2)_2$phenyl, —$(CH_2)_3$phenyl, —$CH(phenyl)_2$, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —$CH_2$pyridinyl, —$CH_2$pyrimidinyl, and the like.

"Heterocycle" (also referred to herein as a "heterocyclic ring") means a 4- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle, such as —CH$_2$morpholinyl, and the like.

"Homocycle" (also referred to herein as "homocyclic ring") means a saturated or unsaturated (but not aromatic) carbocyclic ring containing from 3–7 carbon atoms, such as cyclopropane, cyclobutane, cyclopentane, cyclohexane, cycloheptane, cyclohexene, and the like.

The term "substituted" as used herein means any of the above groups (i.e., alkyl, aryl, arylalkyl, heteroaryl, heteroarylalkyl, homocycle, heterocycle and/or heterocyclealkyl) wherein at least one hydrogen atom is replaced with a substituent. In the case of an oxo substituent ("=O") two hydrogen atoms are replaced. When substituted one or more of the above groups are substituted, "substituents" within the context of this invention include halogen, hydroxy, oxo, cyano, nitro, amino, alkylamino, dialkylamino, alkyl, alkoxy, alkylthio, haloalkyl, aryl, arylalkyl, heteroaryl, heteroarylalkyl, heterocycle and heterocyclealkyl, as well as —NR$_a$R$_b$, —NR$_a$C(=O)R$_b$, —NR$_a$C(=O)NR$_a$NR$_b$, —NR$_a$C(=O)OR$_b$—NR$_a$SO$_2$R$_b$, —C(=O)R$_a$, —C(=O)OR$_a$, —C(=O)NR$_a$R$_b$, —OC(=O)NR$_a$R$_b$, —OR$_a$, —SR$_a$, —SOR$_a$, —S(=O)$_2$R$_a$, —OS(=O)$_2$R$_a$ and —S(=O)$_2$OR$_a$. In addition, the above substituents may be further substituted with one or more of the above substituents, such that the substituent substituted alky, substituted aryl, substituted arylalkyl, substituted heterocycle or substituted heterocyclealkyl. R$_a$ and R$_b$ in this context may be the same or different and independently hydrogen, alkyl, haloalkyl, substituted alkyl, aryl, substituted aryl, arylalkyl, substituted arylalkyl, heterocycle, substituted heterocycle, heterocyclealkyl or substituted heterocyclealkyl.

"Halogen" means fluoro, chloro, bromo and iodo.

"Haloalkyl" means an alkyl having at least one hydrogen atom replaced with halogen, such as trifluoromethyl and the like.

"Alkoxy" means an alkyl moiety attached through an oxygen bridge (i.e., —O-alkyl) such as methoxy, ethoxy, and the like.

"Alkylthio" means an alkyl moiety attached through a sulfur bridge (i.e., —S-alkyl) such as methylthio, ethylthio, and the like.

"Alkylsulfonyl" means an alkyl moiety attached through a sulfonyl bridge (i.e., —SO$_2$-alkyl) such as methylsulfonyl, ethylsulfonyl, and the like.

"Alkylamino" and "dialkylamino" mean one or two alkyl moiety attached through a nitrogen bridge (i.e., —N-alkyl) such as methylamino, ethylamino, dimethylamino, diethylamino, and the like.

With regard to the "R$_1$R$_2$N(CR$_{3a}$R$_{3b}$)$_n$—" moiety of structure (I), n may be 2, 3 or 4. Accordingly, this moiety may be represented by the following structure (i) when n is 2, (ii) when n is 3, and structure (iii) when n is 4:

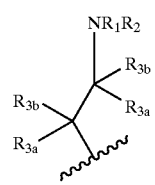

(i)

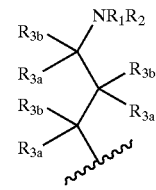

(ii)

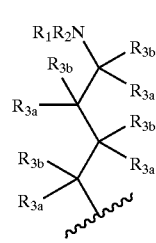

(iii)

wherein each occurrence of R$_{3a}$ and R$_{3b}$ above may be the same or different, and are as defined above. For example, when each occurrence of R$_{3a}$ and R$_{3b}$ in structures (i), (ii) and (iii) is hydrogen, the "R$_1$R$_2$N(CR$_{3a}$R$_{3b}$)$_n$—" moiety has the structure R$_1$R$_2$N(CH$_2$)$_2$—, R$_1$R$_2$N(CH$_2$)$_3$— and R$_1$R$_2$N(CH$_2$)$_4$—, respectively.

The compounds of the present invention may be prepared by known organic synthesis techniques, including the methods described in more detail in the Examples. However in general, the compounds of structure (I) above may be made by the following Reaction Schemes. All substituents in the following Reaction Schemes are as defined above unless indicated otherwise.

Reaction Scheme A

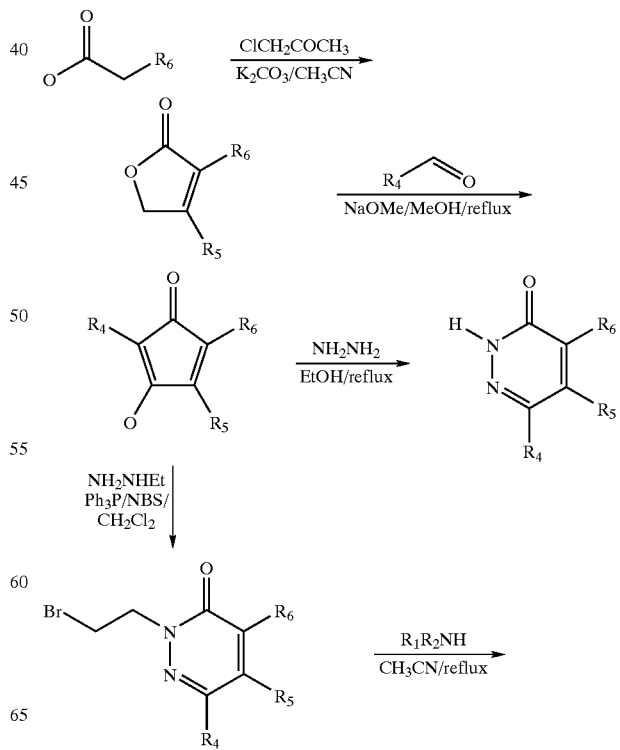

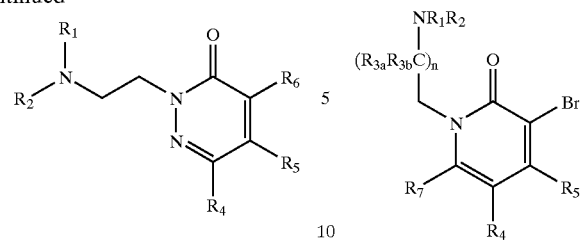
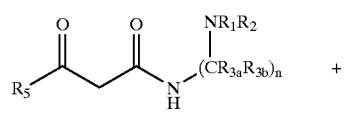
Reaction Scheme B
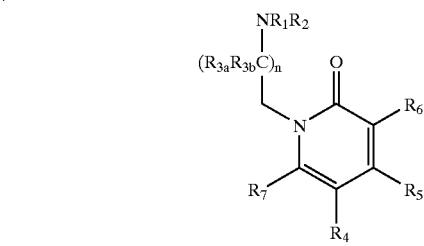
Suzuki coupling $R_6B(OH)_2$
————————————————
DME, $H_2O$, $Ba(OH)_2$, $Pd(Ph_3P)_4$
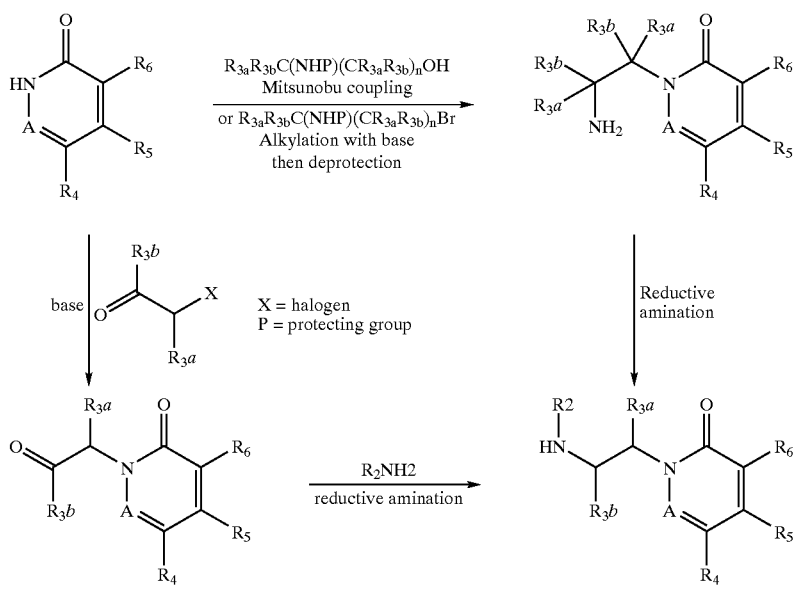
Reaction Scheme C
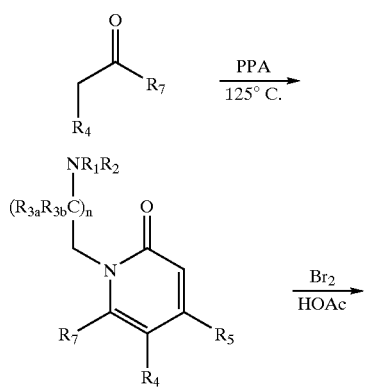
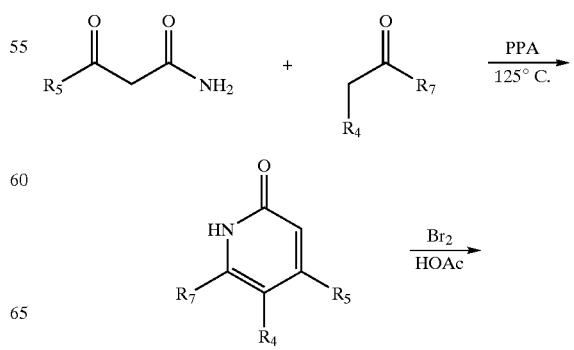
Reaction Scheme D -continued

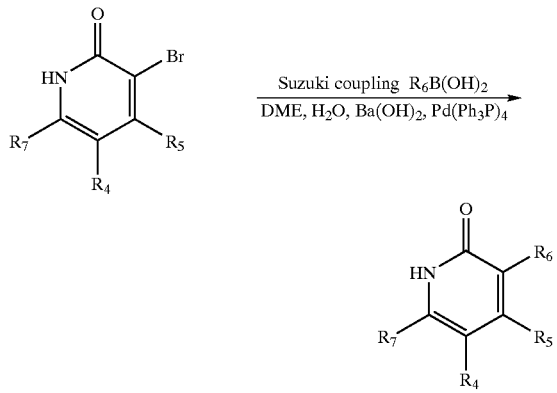

The compounds of structure (I) may generally be referred to as substituted 2H-pyridazin-3-one and 1H-pyridin-2-one compounds, representative compounds of which include the following:

2-(2-Amino-2-phenyl-ethyl)-6-(2,6-difluoro-benzyl)-4-(2-fluoro-3-methoxy-phenyl)-5-methyl-2H-pyridazin-3-one;
2-(2-Amino-2-phenyl-ethyl)-6-(2,6-dichloro-benzyl)-4-(2-fluoro-3-methoxy-phenyl)-5-methyl-2H-pyridazin-3-one;
2-(2-Amino-2-phenyl-ethyl)-6-(2-fluoro-6-chloro-benzyl)-4-(2-fluoro-3-methoxy-phenyl)-5-methyl-2H-pyridazin-3-one;
2-(2-Amino-2-phenyl-ethyl)-6-(2-fluoro-6-trifluoromethyl-benzyl)-4-(2-fluoro-3-methoxy-phenyl)-5-methyl-2H-pyridazin-3-one;
2-(2-Amino-2-phenyl-ethyl)-6-(2-fluoro-6-methylsulfonyl-benzyl)-4-(2-fluoro-3-methoxy-phenyl)-5-methyl-2H-pyridazin-3-one;
2-(2-Amino-2-phenyl-ethyl)-6-(2-fluoro-benzyl)-4-(2-fluoro-3-methoxy-phenyl)-5-methyl-2H-pyridazin-3-one;
2-(2-Amino-2-phenyl-ethyl)-6-(2-chloro-benzyl)-4-(2-fluoro-3-methoxy-phenyl)-5-methyl-2H-pyridazin-3-one;
2-(2-Amino-2-phenyl-ethyl)-6-(2-trifluoromethyl-benzyl)-4-(2-fluoro-3-methoxy-phenyl)-5-methyl-2H-pyridazin-3-one;
2-(2-Amino-2-phenyl-ethyl)-6-(2-methyl sulfonyl-benzyl)-4-(2-fluoro-3-methoxy-phenyl)-5-methyl-2H-pyridazin-3-one;
2-(2-Amino-2-phenyl-ethyl)-6-(2,6-difluoro-benzyl)-4-(2-fluoro-phenyl)-5-methyl-2H-pyridazin-3-one;
2-(2-Amino-2-phenyl-ethyl)-6-(2,6-dichloro-benzyl)-4-(2-fluoro-phenyl)-5-methyl-2H-pyridazin-3-one;
2-(2-Amino-2-phenyl-ethyl)-6-(2-fluoro-6-chloro-benzyl)-4-(2-fluoro-phenyl)-5-methyl-2H-pyridazin-3-one;
2-(2-Amino-2-phenyl-ethyl)-6-(2-fluoro-6-trifluoromethyl-benzyl)-4-(2-fluoro-phenyl)-5-methyl-2H-pyridazin-3-one;
2-(2-Amino-2-phenyl-ethyl)-6-(2-fluoro-6-methylsulfonyl-benzyl)-4-(2-fluoro-phenyl)-5-methyl-2H-pyridazin-3-one;
2-(2-Amino-2-phenyl-ethyl)-6-(2-fluoro-benzyl)-4-(2-fluoro-phenyl)-5-methyl-2H-pyridazin-3-one;
2-(2-Amino-2-phenyl-ethyl)-6-(2-chloro-benzyl)-4-(2-fluoro-phenyl)-5-methyl-2H-pyridazin-3-one;
2-(2-Amino-2-phenyl-ethyl)-6-(2-trifluoromethyl-benzyl)-4-(2-fluoro-phenyl)-5-methyl-2H-pyridazin-3-one;
2-(2-Amino-2-phenyl-ethyl)-6-(2-methylsulfonyl-benzyl)-4-(2-fluoro-phenyl)-5-methyl-2H-pyridazin-3-one;
2-(2-Amino-2-phenyl-ethy)-6-(2,6-difluoro-benzyl)-4-(2-chloro-phenyl)-5-methyl-2H-pyridazin-3-one;
2-(2-Amino-2-phenyl-ethyl)-6-(2,6-dichloro-benzyl)-4-(2-chloro-phenyl)-5-methyl-2H-pyridazin-3-one;
2-(2-Amino-2-phenyl-ethyl)-6-(2-fluoro-6-chloro-benzyl)-4-(2-chloro-phenyl)-5-methyl-2H-pyridazin-3-one;
2-(2-Amino-2-phenyl-ethyl)-6-(2-fluoro-6-trifluoromethyl-benzyl)-4-(2-chloro-phenyl)-5-methyl-2H-pyridazin-3-one;
2-(2-Amino-2-phenyl-ethyl)-6-(2-fluoro-6-methylsulfonyl-benzyl)-4-(2-chloro-phenyl)-5-methyl-2H-pyridazin-3-one;
2-(2-Amino-2-phenyl-ethyl)-6-(2-fluoro-benzyl)-4-(2-chloro-phenyl)-5-methyl-2H-pyridazin-3-one;
2-(2-Amino-2-phenyl-ethyl)-6-(2-chloro-benzyl)-4-(2-chloro-phenyl)-5-methyl-2H-pyridazin-3-one;
2-(2-Amino-2-phenyl-ethyl)-6-(2-trifluoromethyl-benzyl)-4-(2-chloro-phenyl)-5-methyl-2H-pyridazin-3-one;
2-(2-Amino-2-phenyl-ethyl)-6-(2-methylsulfonyl-benzyl)-4-(2-chloro-phenyl)-5-methyl-2H-pyridazin-3-one;
2-(2-Amino-2-phenyl-ethyl)-6-(2,6-difluoro-benzyl)-4-(3-methoxy-phenyl)-5-methyl-2H-pyridazin-3-one;
2-(2-Amino-2-phenyl-ethyl)-6-(2,6-dichloro-benzyl)-4-(3-methoxy-phenyl)-5-methyl-2H-pyridazin-3-one;
2-(2-Amino-2-phenyl-ethyl)-6-(2-fluoro-6-chloro-benzyl)-4-(3-methoxy-phenyl)-5-methyl-2H-pyridazin-3-one;
2-(2-Amino-2-phenyl-ethyl)-6-(2-fluoro-6-trifluoromethyl-benzyl)-4-(3-methoxy-phenyl)-5-methyl-2H-pyridazin-3-one;
2-(2-Amino-2-phenyl-ethyl)-6-(2-fluoro-6-methylsulfonyl-benzyl)-4-(3-methoxy-phenyl)-5-methyl-2H-pyridazin-3-one;
2-(2-Amino-2-phenyl-ethyl)-6-(2-fluoro-benzyl)-4-(3-methoxy-phenyl)-5-methyl-2H-pyridazin-3-one;
2-(2-Amino-2-phenyl-ethyl)-6-(2-chloro-benzyl)-4-(3-methoxy-phenyl)-5-methyl-2H-pyridazin-3-one;
2-(2-Amino-2-phenyl-ethyl)-6-(2-trifluoromethyl-benzyl)-4-(3-methoxy-phenyl)-5-methyl-2H-pyridazin-3-one;
2-(2-Amino-2-phenyl-ethyl)-6-(2-methylsulfonyl-benzyl)-4-(3-methoxy-phenyl)-5-methyl-2H-pyridazin-3-one;
2-(2-Amino-2-phenyl-ethyl)-6-(2,6-difluoro-benzyl)-4-(2-chloro-3-methoxy-phenyl)-5-methyl-2H-pyridazin-3-one;
2-(2-Amino-2-phenyl-ethyl)-6-(2,6-dichloro-benzyl)-4-(2-chloro-3-methoxy-phenyl)-5-methyl-2H-pyridazin-3-one;
2-(2-Amino-2-phenyl-ethyl)-6-(2-fluoro-6-chloro-benzyl)-4-(2-chloro-3-methoxy-phenyl)-5-methyl-2H-pyridazin-3-one;
2-(2-Amino-2-phenyl-ethyl)-6-(2-fluoro-6-trifluoromethyl-benzyl)-4-(2-chloro-3-methoxy-phenyl)-5-methyl-2H-pyridazin-3-one;
2-(2-Amino-2-phenyl-ethyl)-6-(2-fluoro-6-methylsulfonyl-benzyl)-4-(2-chloro-3-methoxy-phenyl)-5-methyl-2H-pyridazin-3-one;
2-(2-Amino-2-phenyl-ethyl)-6-(2-fluoro-benzyl)-4-(2-chloro-3-methoxy-phenyl)-5-methyl-2H-pyridazin-3-one;
2-(2-Amino-2-phenyl-ethyl)-6-(2-chloro-benzyl)-4-(2-chloro-3-methoxy-phenyl)-5-methyl-2H-pyridazin-3-one;
2-(2-Amino-2-phenyl-ethyl)-6-(2-trifluoromethyl-benzyl)-4-(2-chloro-3-methoxy-phenyl)-5-methyl-2H-pyridazin-3-one;
2-(2-Amino-2-phenyl-ethyl)-6-(2-methylsulfonyl-benzyl)-4-(2-chloro-3-methoxy-phenyl)-5-methyl-2H-pyridazin-3-one;
1-(2-Amino-2-phenyl-ethyl)-5-(2,6-difluoro-benzyl)-3-(2-fluoro-3-methoxy-phenyl)-4,6-dimethyl-1H-pyridin-2-one;
1-(2-Amino-2-phenyl-ethyl)-5-(2,6-dichloro-benzyl)-3-(2-fluoro-3-methoxy-phenyl)-4,6-dimethyl-1H-pyridin-2-one;

1-(2-Amino-2-phenyl-ethyl)-5-(2-fluoro-6-chloro-benzyl)-3-(2-fluoro-3-methoxy-phenyl)-4,6-dimethyl-1H-pyridin-2-one;

1-(2-Amino-2-phenyl-ethyl)-5-(2-fluoro-6-trifluoromethyl-benzyl)-3-(2-fluoro-3-methoxy-phenyl)-4,6-dimethyl-1H-pyridin-2-one;

1-(2-Amino-2-phenyl-ethyl)-5-(2-fluoro-6-methylsulfonyl-benzyl)-3-(2-fluoro-3-methoxy-phenyl)-4,6-dimethyl-1H-pyridin-2-one;

1-(2-Amino-2-phenyl-ethyl)-5-(2-fluoro-benzyl)-3-(2-fluoro-3-methoxy-phenyl)-4,6-dimethyl-1H-pyridin-2-one;

1-(2-Amino-2-phenyl-ethyl)-5-(2-chloro-benzyl)-3-(2-fluoro-3-methoxy-phenyl)-4,6-dimethyl-1H-pyridin-2-one;

1-(2-Amino-2-phenyl-ethyl)-5-(2-trifluoromethyl-benzyl)-3-(2-fluoro-3-methoxy-phenyl)-4,6-dimethyl-1H-pyridin-2-one;

1-(2-Amino-2-phenyl-ethyl)-5-(2-methylsulfonyl-benzyl)-3-(2-fluoro-3-methoxy-phenyl)-4,6-dimethyl-1H-pyridin-2-one;

1-(2-Amino-2-phenyl-ethyl)-5-(2,6-difluoro-benzyl)-3-(2-fluoro-phenyl)-4,6-dimethyl-1H-pyridin-2-one;

1-(2-Amino-2-phenyl-ethyl)-5-(2,6-dichloro-benzyl)-3-(2-fluoro-phenyl)-4,6-dimethyl-1H-pyridin-2-one;

1-(2-Amino-2-phenyl-ethyl)-5-(2-fluoro-6-chloro-benzyl)-3-(2-fluoro-phenyl)-4,6-dimethyl-1H-pyridin-2-one;

1-(2-Amino-2-phenyl-ethyl)-5-(2-fluoro-6-trifluoromethyl-benzyl)-3-(2-fluoro-phenyl)-4,6-dimethyl-1H-pyridin-2-one;

1-(2-Amino-2-phenyl-ethyl)-5-(2-fluoro-6-methylsulfonyl-benzyl)-3-(2-fluoro-phenyl)-4,6-dimethyl-1H-pyridin-2-one;

1-(2-Amino-2-phenyl-ethyl)-5-(2-fluoro-benzyl)-3-(2-fluoro-phenyl)-4,6-dimethyl-1H-pyridin-2-one;

1-(2-Amino-2-phenyl-ethyl)-5-(2-chloro-benzyl)-3-(2-fluoro-phenyl)-4,6-dimethyl-1H-pyridin-2-one;

1-(2-Amino-2-phenyl-ethyl)-5-(2-trifluoromethyl-benzyl)-3-(2-fluoro-phenyl)-4,6-dimethyl-1H-pyridin-2-one;

1-(2-Amino-2-phenyl-ethyl)-5-(2-methylsulfonyl-benzyl)-3-(2-fluoro-phenyl)-4,6-dimethyl-1H-pyridin-2-one;

1-(2-Amino-2-phenyl-ethyl)-5-(2,6-difluoro-benzyl)-3-(2-chloro-phenyl)-4,6-dimethyl-1H-pyridin-2-one;

1-(2-Amino-2-phenyl-ethyl)-5-(2,6-dichloro-benzyl)-3-(2-chloro-phenyl)-4,6-dimethyl-1H-pyridin-2-one;

1-(2-Amino-2-phenyl-ethyl)-5-(2-fluoro-6-chloro-benzyl)-3-(2-chloro-phenyl)-4,6-dimethyl-1H-pyridin-2-one;

1-(2-Amino-2-phenyl-ethyl)-5-(2-fluoro-6-trifluoromethyl-benzyl)-3-(2-chloro-phenyl)-4,6-dimethyl-1H-pyridin-2-one;

1-(2-Amino-2-phenyl-ethyl)-5-(2-fluoro-6-methylsulfonyl-benzyl)-3-(2-chloro-phenyl)-4,6-dimethyl-1H-pyridin-2-one;

1-(2-Amino-2-phenyl-ethyl)-5-(2-fluoro-benzyl)-3-(2-chloro-phenyl)-4,6-dimethyl-1H-pyridin-2-one;

1-(2-Amino-2-phenyl-ethyl)-5-(2-chloro-benzyl)-3-(2-chloro-phenyl)-4,6-dimethyl-1H-pyridin-2-one;

1-(2-Amino-2-phenyl-ethyl)-5-(2-trifluoromethyl-benzyl)-3-(2-chloro-phenyl)-4,6-dimethyl-1H-pyridin-2-one;

1-(2-Amino-2-phenyl-ethyl)-5-(2-methylsulfonyl-benzyl)-3-(2-chloro-phenyl)-4,6-dimethyl-1H-pyridin-2-one;

1-(2-Amino-2-phenyl-ethyl)-5-(2,6-difluoro-benzyl)-3-(3-methoxy-phenyl)-4,6-dimethyl-1H-pyridin-2-one;

1-(2-Amino-2-phenyl-ethyl)-5-(2,6-dichloro-benzyl)-3-(3-methoxy-phenyl)-4,6-dimethyl-1H-pyridin-2-one;

1-(2-Amino-2-phenyl-ethyl)-5-(2-fluoro-6-chloro-benzyl)-3-(3-methoxy-phenyl)-4,6-dimethyl-1H-pyridin-2-one;

1-(2-Amino-2-phenyl-ethyl)-5-(2-fluoro-6-trifluoromethyl-benzyl)-3-(3-methoxy-phenyl)-4,6-dimethyl-1H-pyridin-2-one;

1-(2-Amino-2-phenyl-ethyl)-5-(2-fluoro-6-methylsulfonyl-benzyl)-3-(3-methoxy-phenyl)-4,6-dimethyl-1H-pyridin-2-one;

1-(2-Amino-2-phenyl-ethyl)-5-(2-fluoro-benzyl)-3-(3-methoxy-phenyl)-4,6-dimethyl-1H-pyridin-2-one;

1-(2-Amino-2-phenyl-ethyl)-5-(2-chloro-benzyl)-3-(3-methoxy-phenyl)-4,6-dimethyl-1H-pyridin-2-one;

1-(2-Amino-2-phenyl-ethyl)-5-(2-trifluoromethyl-benzyl)-3-(3-methoxy-phenyl)-4,6-dimethyl-1H-pyridin-2-one;

1-(2-Amino-2-phenyl-ethyl)-5-(2-methylsulfonyl-benzyl)-3-(3-methoxy-phenyl)-4,6-dimethyl-1H-pyridin-2-one;

1-(2-Amino-2-phenyl-ethyl)-5-(2,6-difluoro-benzyl)-3-(2-chloro-3-methoxy-phenyl)-4,6-dimethyl-1H-pyridin-2-one;

1-(2-Amino-2-phenyl-ethyl)-5-(2,6-dichloro-benzyl)-3-(2-chloro-3-methoxy-phenyl)-4,6-dimethyl-1H-pyridin-2-one;

1-(2-Amino-2-phenyl-ethyl)-5-(2-fluoro-6-chloro-benzyl)-3-(2-chloro-3-methoxy-phenyl)-4,6-dimethyl-1H-pyridin-2-one;

1-(2-Amino-2-phenyl-ethyl)-5-(2-fluoro-6-trifluoromethyl-benzyl)-3-(2-chloro-3-methoxy-phenyl)-4,6-dimethyl-1H-pyridin-2-one;

1-(2-Amino-2-phenyl-ethyl)-5-(2-fluoro-6-methylsulfonyl-benzyl)-3-(2-chloro-3-methoxy-phenyl)-4,6-dimethyl-1H-pyridin-2-one;

1-(2-Amino-2-phenyl-ethyl)-5-(2-fluoro-benzyl)-3-(2-chloro-3-methoxy-phenyl)-4,6-dimethyl-1H-pyridin-2-one;

1-(2-Amino-2-phenyl-ethyl)-5-(2-chloro-benzyl)-3-(2-chloro-3-methoxy-phenyl)-4,6-dimethyl-1H-pyridin-2-one;

1-(2-Amino-2-phenyl-ethyl)-5-(2-trifluoromethyl-benzyl)-3-(2-chloro-3-methoxy-phenyl)-4,6-dimethyl-1H-pyridin-2-one; and 1-(2-Amino-2-phenyl-ethyl)-5-(2-methylsulfonyl-benzyl)-3-(2-chloro-3-methoxy-phenyl)-4,6-dimethyl-1H-pyridin-2-one.

In addition, representative compounds of the present invention also include those compounds where the primary amine of the above named compounds is substituted with a substituted alkyl group or a cycloalkyl group. As described in the examples, one method of alkylating amines and amides is by reductive alkylation. There are many alternative methods well known in the chemical arts for accomplishing the reductive alkylation procedure, and there are many alternative alkylation methods. When an aldehyde, ketone, carboxylic acid, or acid chloride is treated with a primary or secondary amine in the presence of a reducing agent reductive alkylation may take place. Suitable reducing agents include (but are not limited to) sodium borohydride, sodium triacetoxyborohydride, sodium cyanoborohydride, hydrogen gas and a hydrogenation catalyst, zinc and hydrochloric acid, iron pentacarbonyl and alcoholic potassium hydroxide, formic acid, pyridine borohydride. Amines and amides may also be alkylated by the reaction of formaldehyde and a Mannich base or by the nucleophilic displacement of an alkyl halide or other leaving groups. As an example, the Mitsunobu reaction allows the alkylation of amines with primary or secondary alcohols and carboxylic acids by activation of the hydroxyl group with triphenylphoshine to form the leaving group triphenylphoshine oxide. Other commonly used alkylation methods are described in March, Advanced Organic Chemistry, 4th Ed., pp 1276–1277 (1992).

The compounds of the present invention may generally be utilized as the free acid or free base. Alternatively, the compounds of this invention may be used in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylanmonium, and the like). Thus, the term "pharmaceutically acceptable salt" of structure (I) is intended to encompass any and all acceptable salt forms.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfydryl groups. Thus, representative examples of prodrugs include (but are not limited to) acetate, formate and benzoate derivatives of alcohol and amine functional groups of the compounds of structure (I). Further, in the case of a carboxylic acid (—COOH), esters may be employed, such as methyl esters, ethyl esters, and the like.

With regard to stereoisomers, the compounds of structure (I) may have chiral centers and may occur as racemates, racemic mixtures and as individual enantiomers or diastereomers. Compounds of structure (I) may also possess axial chirality, which may result in atropisomers. All such isomeric forms are included within the present invention, including mixtures thereof. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

The effectiveness of a compound as a GnRH receptor antagonist may be determined by various assay methods. Suitable GNRH antagonists of this invention are capable of inhibiting the specific binding of GnRH to its receptor and antagonizing activities associated with GNRH. For example, inhibition of GNRH stimulated LH release in immature rats may be measured according to the method of Vilchez-Martinez (Endocrinology 96:1130–1134, 1975). Briefly, twenty-five day old male Sprague-Dawley rats are administered an GNRH antagonist in saline or other suitable formulation by oral gavage, sub-cutaneous injection, or intravenous injection. This is followed by sub-cutaneous injection of 200 ng GnRH in 0.2 ml saline. Thirty minutes after the last injection, the animals are decapitated and trunk blood collected. After centrifugation, the separated plasma is stored at −20° C. until determination of the LH and FSH by radioimmunoassay. Other techniques for determining the activity of GnRH receptor antagonists are well known in the field, such as the use of cultured pituitary cells for measuring GNRH activity (Vale et al., *Endocrinology* 91:562–572, 1972), and a technique for measuring radioligand binding to rat pituitary membranes (Perrin et al., *Mol. Pharmacol.* 23:44–51, 1983).

For example, effectiveness of a compound as a GnRH receptor antagonist may be determined by one or more of the following assays.

Rat Anterior Pituitary Cell Culture Assay of GnRH Antagonists

Anterior pituitary glands are collected from 7-week-old female Sprague-Dawley rats and the harvested glands digested with collagenase in a dispersion flask for 1.5 hr at 37° C. After collagenase digestion, the glands are further digested with neuraminidase for 9 min at 37° C. The digested tissue is then washed with 0.1% BSA/McCoy's 5A medium, and the washed cells suspended in 3% FBS/0.1 BSA/McCoy's 5A medium and plated into 96-well tissue culture plates at a cell density of 40,000 cells per well in 200 $\mu$l medium. The cells are then incubated at 37° C. for 3 days. One pituitary gland normally yields one 96-well plate of cells, which can be used for assaying three compounds. For assay of an GnRH antagonist, the incubated cells are first washed with 0.1% BSA/McCoy's 5A medium once, followed by addition of the test sample plus 1 nM GNRH in 200 $\mu$l 0.1% BSA/McCoy's 5A medium in triplicate wells. Each sample is assayed at 5-dose levels to generate a dose-response curve for determination of its potency on the inhibition of GNRH stimulated LH and/or FSH release. After 4-hr incubation at 37° C., the medium is harvested and the level of LH and/or FSH secreted into the medium determined by RIA.

RIA of LH and FSH

For determination of the LH levels, each sample medium is assayed in duplicates and all dilutions are done with RIA buffer (0.01M sodium phosphate buffer/0.15M NaCl/1% BSA/0.01% NaN3, pH 7.5) and the assay kit is obtained from the Nation Hormone and Pituitary Program supported by NIDDK. To a 12×75 mm polyethylene test tube is added 100 $\mu$l of sample medium diluted 1:5 or rLH standard in RIA buffer and 100 $\mu$l of [125I]-labeled rLH (~30,000 cpm) plus 100 $\mu$l of rabbit anti-rLH antibody diluted 1:187,500 and 100 $\mu$l RIA buffer. The mixture is incubated at room temperature over-night. In the next day, 100 $\mu$l of goat anti-rabbit IgG diluted 1:20 and 100 $\mu$l of normal rabbit serum diluted 1:1000 are added and the mixture incubated for another 3 hr at room temperature. The incubated tubes are then centrifuged at 3,000 rpm for 30 min and the supernatant removed by suction. The remaining pellet in the tubes is counted in a gamma-counter. RIA of FSH is done in a similar fashion as the assay for LH with substitution of the LH antibody by the FSH antibody diluted 1:30,000 and the labeled rLH by the labeled rFSH.

Radio-Iodination of GnRH Peptide

The GNRH analog is labeled by the chloramine-T method. To 10 $\mu$g of peptide in 20 $\mu$l of 0.5M sodium phosphate buffer, pH 7.6, is added 1 mCi of Na125I, followed by 22.5 $\mu$g chloramine-T and the mixture vortexed for 20 sec. The reaction is stopped by the addition of 60 $\mu$g sodium metabisulfite and the free iodine is removed by passing the iodinated mixture through a C-8 Sep-Pak cartridge (Millipore Corp., Milford, Mass.). The peptide is eluted with a small volume of 80% acetonitrile/water. The recovered labeled peptide is further purified by reverse phase HPLC on a Vydac C-18 analytical column (The Separations Group, Hesperia, Calif.) on a Beckman 334 gradient HPLC system using a gradient of acetonitrile in 0.1% TFA. The purified radioactive peptide is stored in 0.1% BSA/20% acetonitrile/0.1% TFA at −80° C. and can be used for up to 4 weeks.

GnRH Receptor Membrane Binding Assay

Cells stably, or transiently, transfected with GnRH receptor expression vectors are harvested, resuspended in 5% sucrose and homogenized using a polytron homogenizer (2×15 sec). Nucleii are removed by centrifugation (3000×g for 5 min.), and the supernatant centrifuged (20,000×g for 30 min, 4° C.) to collect the membrane fraction. The final membrane preparation is resuspended in binding buffer (10 mM Hepes (pH 7.5), 150 mM NaCl, and 0.1% BSA) and stored at −70° C. Binding reactions are performed in a Millipore MultiScreen 96-well filtration plate assembly with polyethylenimine coated GF/C membranes. The reaction is initiated by adding membranes (40 ug protein in 130 ul binding buffer) to 50 ul of [$^{125}$I]-labeled GNRH peptide (~100,000 cpm), and 20 ul of competitor at varying concentrations. The reaction is terminated after 90 minutes by application of vacuum and washing (2×) with phosphate buffered saline. Bound radioactivity is measured using 96-well scintillation counting (Packard Topcount) or by removing the filters from the plate and direct gamma counting. $K_i$ values are calculated from competition binding data using non-linear least squares regression using the Prism software package (GraphPad Software).

Activity of GnRH receptor antagonists are typically calculated from the $IC_{50}$ as the concentration of a compound necessary to displace 50% of the radiolabeled ligand from the GnRH receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973). GnRH receptor antagonists of this invention have a $K_i$ of 100 μM or less. In a preferred embodiment of this invention, the GnRH receptor antagonists have a $K_i$ of less than 10 μM, and more preferably less than 1 μM, and even more preferably less than 0.1 μM (i.e., 100 nM).

As mentioned above, the GnRH receptor antagonists of this invention have utility over a wide range of therapeutic applications, and may be used to treat a variety of sex-hormone related conditions in both men and women, as well as mammals in general. For example, such conditions include endometriosis, uterine fibroids, polycystic ovarian disease, hirsutism, precocious puberty, gonadal steroid-dependent neoplasia such as cancers of the prostate, breast and ovary, gonadotrophe pituitary adenomas, sleep apnea, irritable bowel syndrome, premenstrual syndrome, benign prostatic hypertrophy, contraception and infertility (e.g., assisted reproductive therapy such as in vitro fertilization).

The compounds of this invention are also useful as an adjunct to treatment of growth hormone deficiency and short stature, and for the treatment of systemic lupus erythematosis.

In addition, the compounds are useful in combination with androgens, estrogens, progesterones, and antiestrogens and antiprogestogens for the treatment of endometriosis, fibroids, and in contraception, as well as in combination with an angiotensin-converting enzyme inhibitor, an angiotensin II-receptor antagonist, or a renin inhibitor for the treatment of uterine fibroids. The compounds may also be used in combination with bisphosphonates and other agents for the treatment and/or prevention of disturbances of calcium, phosphate and bone metabolism, and in combination with estrogens, progesterones and/or androgens for the prevention or treatment of bone loss or hypogonadal symptoms such as hot flashes during therapy with a GnRH antagonist.

In another embodiment of the invention, pharmaceutical compositions containing one or more GnRH receptor antagonists are disclosed. For the purposes of administration, the compounds of the present invention may be formulated as pharmaceutical compositions. Pharmaceutical compositions of the present invention comprise a GnRH receptor antagonist of the present invention and a pharmaceutically acceptable carrier and/or diluent. The GnRH receptor antagonist is present in the composition in an amount that is effective to treat a particular disorder—that is, in an amount sufficient to achieve GnRH receptor antagonist activity, and preferably with acceptable toxicity to the patient. Typically, the pharmaceutical compositions of the present invention may include a GnRH receptor antagonist in an amount from 0.1 mg to 250 mg per dosage depending upon the route of administration, and more typically from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets that contain, in addition to a GNRH receptor antagonist, diluents, dispersing and surface active agents, binders, and lubricants. One skilled in this art may further formulate the GnRH receptor antagonist in an appropriate manner, and in accordance with accepted practices, such as those disclosed in *Remington's Pharmaceutical Sciences*, Gennaro, Ed., Mack Publishing Co., Easton, Pa. 1990.

In another embodiment, the present invention provides a method for treating sex-hormone related conditions as discussed above. Such methods include administering of a compound of the present invention to a warm-blooded animal in an amount sufficient to treat the condition. In this context, "treat" includes prophylactic administration. Such methods include systemic administration of a GnRH receptor antagonist of this invention, preferably in the form of a pharmaceutical composition as discussed above. As used herein, systemic administration includes oral and parenteral methods of administration. For oral administration, suitable pharmaceutical compositions of GnRH receptor antagonists include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain, in addition to the GnRH receptor antagonist, buffers, antioxidants, bacteriostats, and other additives commonly employed in such solutions.

The following example is provided for purposes of illustration, not limitation. In summary, the GnRH receptor antagonists of this invention may be assayed by the general methods disclosed above, while the following Examples disclose the synthesis of representative compounds of this invention.

EXAMPLE 1

SYNTHESIS OF 4-(3-METHOXYPHENYL)-5-METHYL-6-(2-FLUOROBENZYL)-2-[N-(2-PYRIDYL)ETHYL-N-METHYL]ETHYL-PYRIDAZIN-3-ONE

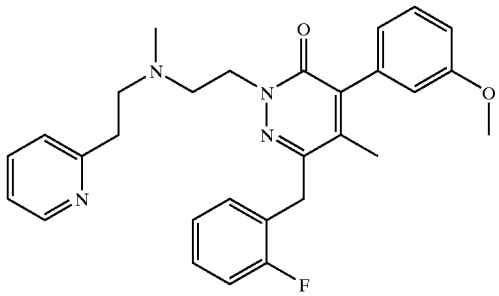

Step 1A 3-(3-Methoxyphenyl)-4-methyl-2(5H)-furanone

A mixture of 3-methoxyphenylacetic acid (3.32 g, 20 mmol), chloroacetone (2.02 g, 22 mmol) and potassium carbonate (6.07 g, 44 mmol) in acetonitrile (30 mL) was heated at reflux for 5 hours. The resultant mixture was cooled to room temperature, diluted with ethyl acetate (60 ml), filtered through a silica gel pad, and washed with ethyl acetate (2×50 mL). The filtrate was concentrated in vacuo and the residue was treated with ether and hexanes to give a yellowish solid (3.2 g, 78% yield). $^1$H NMR (CDCl$_3$):2.22 (s, 3H), 3.84 (s, 3H), 4.79 (s, 2H), 6.92 (m, 1H), 7.05 (m, 2H), 7.36 (m, 1H).

Step 1 B 2-(2-fluorophenyl)-3-hydroxy-4-methyl-5-(3-methoxyphenyl)-2,4-cyclopentadienone A solution of 3-(3-methoxyphenyl)-4-methyl-2(5H)-furanone (2.02 g, 10 mmol) and 2-fluorobenzyladehyde (1.36 g, 11 mmol) in methanol (20 mL) was treated with sodium methoxide (0.6 g, 11 mmol) at room temperature. This mixture was stirred for 15 minutes and then heated at reflux for 3 hours, cooled and poured into ice-water (40 mL). The product was extracted with ethyl acetate (2×100 mL), the extracted was washed with brine, dried over MgSO$_4$, filtered and concentrated in vacuo. The residue was treated with ether to precipitate a yellow solid (1.5 g, 50% yield). $^1$H NMR (CDCl$_3$): 2.39 (s, 3H), 3.86 (s, 3H), 6.46 (s, 1H), 6.95 (m, 1H), 7.05–7.46 (m, 5H), 8.40 (m, 1H); MS: 311 (MH$^+$).

Step 1 C 4-(3-methoxyphenyl)-5-methyl-6-(2-fluorobenzyl)-2H-pyridazin-3-one

A solution of 2-(2-fluorophenyl)-3-hydroxy-4-methyl-5-(3-methoxyphenyl)-2,4-cyclopentadienone (310 mg, 1 mmol) and hydrazine (0.2 mL) in ethanol (5 mL) was heated at reflux for 30 minutes. The resulting solution was concentrated in vacuo and the residue was dissolved in dichloromethane, dried over sodium sulfate, filtered and concentrated in vacuo to give the desired compound as a colorless oil. $^1$H NMR (CDCl$_3$): 2.14 (s, 3H), 3.27 (d, J=13.8 Hz, 1H), 3.43 (d, J=13.8 Hz, 1H), 6.70–7.25 (m, 8H); MS: 325 (MH$^+$).

Step 1 D 4-(3-methoxyphenyl)-5-methyl-6-(2-fluorobenzyl)-2-(2-hydroxyethyl)-pyridazin-3-one A solution of 2-(2-fluorophenyl)-3-hydroxy-4-methyl-5-(3-methoxyphenyl)-2,4-cyclopentadienone (620 mg, 2 mmol) and hydroxyethylhydrazine (360 mg, 45 mmol)) in ethanol (5 mL) was heated at reflux for 6 hours. The resulting solution was concentrated in vacuo and the residue was dissolved in ethyl acetate (80 mL), washed with brine, dried over magnesium sulfate, filtered and concentrated in vacuo to give the desired compound as colorless oil. MS: 369 (MH$^+$).

Step 1 E 4-(3-methoxyphenyl)-5-methyl-6-(2-fluorobenzyl)-2-(2-bromoethyl)-pyridazin-3-one A solution of 4-(3-methoxyphenyl)-5-methyl-6-(2-fluorobenzyl)-2-(2-hydroxyethyl)-pyridazin-3-one (from above) and triphenylphospine (570 mg, 22 mmol) in dichloromethane (8 mL) was treated with N-bromosuccinamide (400 mg, 22 mmol) at room temperature for 2 hours. The crude product was used for next step. MS: 431 (MH$^+$).

Step 1 F 4-(3-methoxyphenyl)-5-methyl-6-(2-fluorobenzyl)-2-[N-(2-pirydyl)ethyl-N-methyl]ethyl-pyridazin-3-one A solution of 4-(3-methoxyphenyl)-5-methyl-6-(2-fluorobenzyl)-2-(2-bromoethyl)-pyridazin-3-one (10% from above) was treated with N-(2-pyridyl)ethyl-N-methylamine (27.2 mg, 0.2 mmol) and the mixture was stirred at room temperature overnight. The product was purified on TLC plate (2×) with 1:1 ethyl acetate-hexanes to give title compound. $^1$H NMR (CDCl$_3$): 1.95 (s, 3H), 2.40 (s, 3H), 2.90 (m, 6H), 3.80 (s, 3H), 4.01 (s, 2H), 4.30 (t, J=7.1 Hz, 2H), 6.76 (s, 1H), 6.79 (d, J=7.5 Hz, 1H), 6.90 (dd, J=1.2, 8.0 Hz, 1H), 7.01–7.23 (m, 6H), 7.33 (t, J=8.1 Hz, 1H), 7.55 (t, J=7.5 Hz, 1H), 8.51 (d, J=4.2 Hz, 1H); MS: 487 (MH$^+$).

EXAMPLE 2

SYNTHESIS OF 4,6-DIMETHYL-5-BENZYL-3-(3-METHOXYPHENYL)-1-[(2R)-AMINO-2-PHENETHYL] PYRIDIN-2-ONE

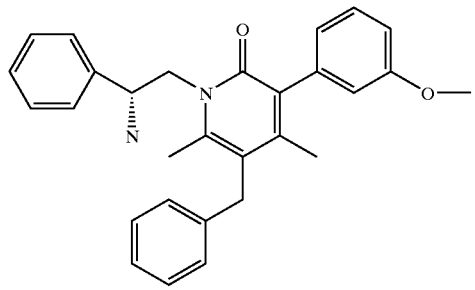

Step 2A 4,6-Dimethyl-5-benzyl-1H-pyridin-2-one

To a mixture of PPA (10 g) and acetoacetamide triethylamine (2.02 g, 20 mmol) was added benzylacetone (5.92 g, 5.98 mL, 40 mmol). The resulting mixture was heated at 125° C. for 3 hours. The brown mixture was poured onto crushed ice and neutralized with solid NaHCO$_3$. The mixture was filtered to give a yellow solid, which was purified by flash column (silica, 10% MeOH/DCM) to give the pyridinone (2.29 g, 53.8%) as a yellow solid. $^1$H NMR (CDCl$_3$) δ 2.07 (s, 3H), 2.37 (s, 3H), 3.81 (s, 2H), 6.38 (s, 1H), 7.00–7.40 (m, 5H); MS (CI) m/z 214.1 (MH$^+$).

Step 2B 4,6-Dimethyl-3-bromo-5-benzol-1H-pyridin-2-one

To a solution of 4,6-dimethyl-5-benzyl-1H-pyridin-2-one (2.21 g, 10.4 mmol) in anhydrous acetic acid (10 mL) was added bromine (3.3 g, 1.06 mL, 20.7 mL). It was stirred at room temperature for one hour. Then the reaction vessel was blew N$_2$ to remove bromine and evaporation removed volatiles. The residue was partitioned between CH$_2$Cl$_2$/sat. NaHCO$_3$/saline (100/50/50 mL). The organic layer was dried over Na$_2$SO$_4$ and evaporation gave the brominated compound as a yellow solid (3.17 g, 100%). $^1$H NMR (CDCl$_3$) δ 2.07 (s, 3H), 2.37 (s, 3H), 3.81 (s, 2H), 7.00–7.40 (m, 5H); MS (CI) m/z 293, 295 (MH$^+$).

Step 2C 4,6-Dimethyl-5-benzyl-3-bromo-1-[(2R)-(tert-butoxycarbonylamino)-2-phenethyl]pyridin-2-one A solution of N-(t-butyloxycarbonyl)-D-α-phenylglycinol (1.02 g, 4.21 mmol) in anhydrous THF (15 mL) was treated with 4,6-dimethyl-3-bromo-5-benzyl-1H-pyridin-2-one (1.25 g, 4.28 mmol) and triphenylphosphine (1.6 g, 6.23 mmol) at ambient temperature, then di-tert-butylazodicarboxylate (1.5 g, 6.5 mmol) was introduced. The reaction mixture was stirred at ambient temperature for 16 h and volatiles were evaporated. The residue was partitioned between sat. NaHCO$_3$ and EtOAc. The organic layer was dried over Na$_2$SO$_4$, evaporated, purified by flash column (silica, 20% EtOAc/Hexane) to give the protected compound as a yellow syrup (0.21 g, 14.8%). MS (CI) m/z 511.1, 514.1 (MH$^+$-Boc).

Step 2D 4,6-dimethyl-5-benzyl-3-(3-methoxyphenyl)-1-F [(2R)-(tert-butoxycarbonylamino)-2-phenethyl]pyridin-2-one 4,6-Dimethyl-5-benzyl-3-bromo-1-[(2R)-(tert-butoxycarbonylamino)-2-phenethyl]pyridin-2-one (0.1 g, 0.2 mmol) in benzene/EtOH/ethylene glycol ether (2/0.2/2.2 mL) was added 3-methoxyphenylboronic acid (38 mg, 0.25 mmol) and saturated Ba(OH)$_2$/water (~0.5 M, 1.5 mL). The reaction mixture was deoxygenated with N$_2$ for 10 min, tetrakis(triphenylphosine) palladium (0) (46.2 mg, 0.04 mmol) was added and the reaction mixture was heated at 80° C. overnight under the protection of N$_2$. The reaction mixture was partitioned between brine and EtOAc. The organic layer was dried over Na$_2$SO$_4$, evaporated, purified by flash column (silica, 30% EtOAc/Hexane) to give the protected compound (0.14 g, 0.26 mmol). MS (CI) m/z 539.2 (MH$^+$).

Step 2E 4,6-Dimethyl-5-benzyl-3-(3-methoxyphenyl)-1-[(2R)-amino)-2-phenethyl]pyridin-2-one A solution of 4,6-dimethyl-5-benzyl-3-(3-methoxyphenyl)-1-[(2R)-(tert-butoxycarbonylamino)-2-phenethyl]pyridin-2-one in DCM (1 mL) was added TFA (1 mL) and the reaction mixture was stirred at ambient temperature for 1 h. Volatiles were evaporated and the residue was dissolved in MeOH (1 mL) and purified by PE-Sciex LCMS to give the title compound (20 mg, 20.4%). MS (CI) m/z 439.2 (MH$^+$).

EXAMPLE 3

SYNTHESIS OF 4,6-DIMETHYL-5-BENZYL-3-(2-FLUORO-3-METHOXYPHENYL)-1-[(2R)-AMINO-2-PHENETHYL]PYRIDIN-2-ONE

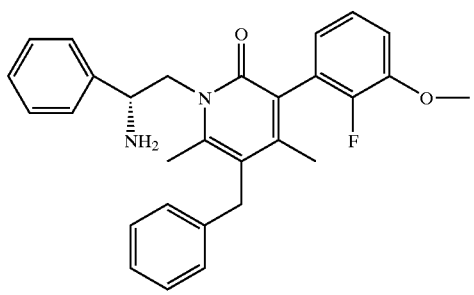

Step 3A 4,6-Dimethyl-5-benzyl-3-(2-fluoro-3-methoxyphenyl)-1-[(2R)-(tert-butoxycarbonylamino)-2-phenethyl]pyridin-2-one 4,6-Dimethyl-5-benzyl-3-bromo-1-[(2R)-(tert-butoxycarbonylamino)-2-phenethyl]pyridin-2-one (from Step 2C, 0.1 g, 0.2 mmol) in benzene/EtOH/ethylene glycol ether (2/0.2/2.2 mL) was added 2-fluoro-3-methoxyphenylboronic acid (40 mg, 0.25 mmol) and saturated Ba(OH)$_2$/water (~0.5 M, 1.5 mL). The reaction mixture was deoxygenated with N$_2$ for 10 min, tetrakis (triphenylphosine) palladium (0) (46.2 mg, 0.04 mmol) was added and the reaction mixture was heated at 80° C. overnight under the protection of N$_2$. The reaction mixture was partitioned between brine and EtOAc. The organic layer was dried over Na$_2$SO$_4$, evaporated, purified by flash column (silica, 30% EtOAc/Hexane) to give the protected compound without further purification. MS (CI) m/z 557.2 (MH$^+$).

Step 3B 4,6-Dimethyl-5-benzyl-3-(2-fluoro-3-methoxyphenyl)-1-[(2R)-amino)-2-phenethyl]pyridin-2-one A solution of 4,6-dimethyl-5-benzyl-3-(2-fluoro-3-methoxyphenyl)-1-[(2R)-(tert -butoxycarbonylamino-2-phenethyl]pyridin-2-one in DCM (1 mL) was added TFA (1 mL) and the reaction mixture was stirred at ambient temperature for 1 h. Volatiles were evaporated and the residue was dissolved in MeOH (1 mL) and purified by PE-Sciex LCMS to give the title compound. MS (CI) m/z 457.2 (MH$^+$).

It will be appreciated that, although specific embodiments of the invention have been described herein for purposes of illustration, various modifications may be made without departing from the spirit and scope of the invention. Accordingly, the invention is not limited except as by the appended claims.

All of the above U.S. patents, U.S. patent application publications, U.S. patent applications, foreign patents, foreign patent applications and non-patent publications referred to int his specification and/or listed in the Application Data Sheet are incorporated herein by reference, in their entirety.

We claim:

1. A compound having the following structure:

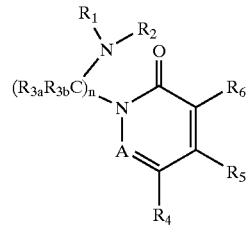

or a stereoisomer, or pharmaceutically acceptable salt thereof, wherein:

A is N;

n is 2, 3 or 4;

$R_1$ and $R_2$ are the same or different and independently hydrogen, alkyl, substituted alkyl, aryl, substituted aryl, arylalkyl, substituted arylalkyl, heterocycle, substituted heterocycle, heterocyclealkyl, substituted heterocyclealkyl, —C(R$_8$)(=NR$_9$) or —C(NR$_{10}$R$_{11}$)(=NR$_9$);

or $R_1$ and $R_2$ taken together with the nitrogen atom to which they are attached form a heterocycle or a substituted heterocycle;

$R_{3a}$ and $R_{3b}$ are the same or different and, at each occurrence, independently hydrogen, alkyl, substituted alkyl, alkoxy, alkylthio, alkylamino, aryl, substituted aryl, arylalkyl, substituted arylalkyl, heterocycle, substituted heterocycle, heterocyclealkyl, substituted heterocyclealkyl, —COOR$_{12}$ or —CONR$_{10}$R$_{11}$;

or $R_{3a}$ and $R_{3b}$ taken together with the carbon atom to which they are attached form a homocycle, substituted homocycle, heterocycle or substituted heterocycle;

or $R_{3a}$ and the carbon to which it is attached taken together with $R_1$ and the nitrogen to which it is attached form a heterocycle or substituted heterocycle;

$R_4$ is arylalkyl, substituted arylalkyl, heteroarylalkyl or substituted heteroarylalkyl;

$R_5$ is hydrogen, alkyl, or substituted alkyl;

$R_6$ is aryl, substituted aryl, heteroaryl, or substituted heteroaryl;

$R_7$ is hydrogen, alkyl, or substituted alkyl;

$R_8$ is independently hydrogen, alkyl, substituted alkyl, aryl, substituted aryl, arylalkyl, substituted arylalkyl, heterocycle, substituted heterocycle, heterocyclealkyl or substituted heterocyclealkyl;

$R_9$ is independently hydrogen, alkyl, substituted alkyl, aryl, substituted aryl, arylalkyl, substituted arylalkyl, heterocycle, substituted heterocycle, heterocyclealkyl or substituted heterocyclealkyl;

$R_{10}$ and $R_{11}$ are the same or different independently hydrogen, alkyl, substituted alkyl, aryl, substituted aryl, arylalkyl, substituted arylalkyl, heterocycle, substituted heterocycle, heterocyclealkyl or substituted heterocyclealkyl; and $R_{12}$ is hydrogen, alkyl, or substituted alkyl.

2. The compound of claim 1 wherein $R_1$ is hydrogen, alkyl, substituted alkyl, arylalkyl, substituted arylalkyl, heterocyclealkyl or substituted heterocyclealkyl.

3. The compound of claim 1 wherein $R_4$ is arylalkyl, substituted arylalkyl, or heteroarylalkyl.

4. The compound of claim 1 wherein $R_6$ is aryl, substituted aryl, or heteroaryl.

5. A pharmaceutical composition comprising a compound of claim 1 and a pharmaceutically acceptable carrier or diluent.

6. A compound according to claim 1, wherein:

n is 2;

$R_{3a}$ is hydrogen at each occurrence;

$R_{3b}$ is hydrogen at one occurrence and aryl or substituted aryl at the other occurrence; and $R_1$ and $R_2$ are independently hydrogen, alkyl or substituted alkyl.

7. A compound according to claim 6, wherein:

$R_{3b}$ is hydrogen at one occurrence and phenyl at the other occurrence; and $R_1$ and $R_2$ are each hydrogen.

8. A compound according to claim 6, wherein $R_5$ is hydrogen or alkyl.

9. A compound according to claim 8, wherein $R_5$ is methyl.

10. A compound according to claim 8, wherein $R_6$ is aryl or substituted aryl.

11. A compound according to claim 10, wherein $R_6$ is phenyl or substituted phenyl.

12. A compound according to claim 11, wherein $R_6$ is 2-fluorophenyl, 2-chlorophenyl, 2-fluoro-3-methoxyphenyl, 2-chloro-3-methoxyphenyl or 3-methoxyphenyl.

13. A compound according to claim 10, wherein $R_4$ is arylalkyl or substituted arylalkyl.

14. A compound according to claim 13, wherein $R_4$ is benzyl or substituted benzyl.

15. A compound according to claim 14, wherein $R_4$ is 2-fluorobenzyl, 2-chlorobenzyl, 2-trifluoromethylbenzyl, 2-methylsulfonylbenzyl, 2,6-difluorobenzyl, 2,6-dichlorobenzyl, 2-fluoro-6-chlorobenzyl, 2-fluoro-6-trifluoromethylbenzyl, or 2-fluoro-6-methylsulfonylbenzyl.

16. A compound according to claim 7, wherein:

$R_4$ is 2-fluorobenzyl, 2-chlorobenzyl, 2-trifluoromethylbenzyl, 2-methylsulfonylbenzyl, 2,6-difluorobenzyl, 2,6-dichlorobenzyl, 2-fluoro-6-chlorobenzyl, 2-fluoro-6-trifluoromethylbenzyl, or 2-fluoro-6-methylsulfonylbenzyl;

$R_5$ is methyl; and $R_6$ is 2-fluorophenyl, 2-chlorophenyl, 2-fluoro-3-methoxyphenyl, 2-chloro-3-methoxyphenyl or 3-methoxyphenyl.

17. A pharmaceutical composition comprising a compound according to claim 6 and a pharmaceutically acceptable carrier or diluent.

18. A pharmaceutical composition according to claim 17, wherein:

$R_{3b}$ is hydrogen at one occurrence and phenyl at the other occurrence; and $R_1$ and $R_2$ are each hydrogen.

19. A pharmaceutical composition comprising a compound according to claim 13 and a pharmaceutically acceptable carrier or diluent.

20. A pharmaceutical composition according to claim 19, wherein:

$R_4$ is 2-fluorobenzyl, 2-chlorobenzyl, 2-trifluoromethylbenzyl, 2-methylsulfonylbenzyl, 2,6-difluorobenzyl, 2,6-dichlorobenzyl, 2-fluoro-6-chlorobenzyl, 2-fluoro-6-trifluoromethylbenzyl, or 2-fluoro-6-methylsulfonylbenzyl;

$R_5$ is methyl; and $R_6$ is 2-fluorophenyl, 2-chlorophenyl, 2-fluoro-3-methoxyphenyl, 2-chloro-3-methoxyphenyl or 3-methoxyphenyl.

* * * * *